US00PP10960P

United States Patent [19]

Lopez

[11] Patent Number: Plant 10,960

[45] Date of Patent: Jun. 15, 1999

[54] STRAWBERRY PLANT NAMED 'TUDNEW'

[75] Inventor: Jose Miguel Arias Lopez, Navarra, Spain

[73] Assignee: Plantas de Navarra S.A., Navarra, Spain

[21] Appl. No.: 08/982,192

[22] Filed: Dec. 1, 1997

[51] Int. Cl.[6] ..... A01H 5/00

[52] U.S. Cl. ..... Plt./208

[58] Field of Search ..... Plt./48, 49, 208, Plt./209

*Primary Examiner*—Howard J. Locker
*Assistant Examiner*—Ashwin D. Mehta
*Attorney, Agent, or Firm*—Christie, Parker & Hale, LLP

[57] ABSTRACT

A strawberry plant producing inflorescence that appears above the foliage and abundant production of red-colored, conical-shaped, firm large fruit.

5 Drawing Sheets

BACKGROUND OF THE INVENTION

The new variety of strawberry was created in a breeding program by crossing two parents from among a group of seedlings which were obtained from a free pollination of 32 different varieties and seedlings; in particular, by crossing as seed parent a variety designed 85-20 and as pollen parent a variety designed 86-061. Both parental varieties are proprietary and have not been commercialized.

The resulting seedling of the new variety was grown and asexually propagated by runners in Soria, Spain, about 3° W, 41° N, 3000 feet evaluation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Tudnew.' Among the characteristics which distinguish the new variety from other varieties are a combination of traits which include inflorescence that appears above the foliage and abundant production of red-colored, conical-shaped, very firm fruit and very large fruit size.

COMPARISON TO CLOSEST VARIETY

The new variety is closest to the variety 'Chandler' (U.S. Plant Pat. No. 5262), but is distinguished therefrom by the following characteristics possessed by 'Tudnew' which are different than, or not possessed by, 'Chandler.'

1. 'Chandler' exhibits more plant vigor than 'Tudnew.'

2. Leaf surface undulation of 'Chandler' is less than in 'Tudnew.'

3. 'Tudnew' has a darker green leaf color than 'Chandler.' The differences in the leaves of 'Chandler' and the new variety are shown in FIG. 7. These differences are maintained during the growing season.

4. In 'Tudnew' the position of the inflorescence relative to foliage is above. In 'Chandler' it is level with the foliage.

5. In 'Tudnew' the petals are as long as broad. In 'Chandler' they are broader than long. The differences in the ratio of length/width of the petals of 'Chandler' and the new variety are shown in FIG. 8. These differences are maintained during the flowering season.

6. 'Chandler' fruit is longer than broad. 'Tudnew' fruit is much longer than broad and very large.

7. 'Chandler' has an almost cylindrical shape. In 'Tudnew' the shape is conical.

8. 'Chandler' has a medium band without achenes and the insertion of achenes is level with surface; whereas, in 'Tudnew' the band without achenes is broad and the insertion is below surface.

9. In 'Chandler' the calyx segments appear clasping or detached; whereas, in 'Tudnew' they are reflexed.

10. 'Chandler' calyx is larger than the fruit, and in 'Tudnew' it is the same size.

11. 'Chandler' fruit is less firm than 'Tudnew' fruit.

BRIEF DESCRIPTION OF ILLUSTRATIONS

The accompanying photographs show typical specimens of the new variety, designated 92.H1.51 in the illustrations, including fruit, foliage and flower, in color as nearly true as it is reasonably possible to make in color illustrations of this character.

DESCRIPTION OF THE NEW VARIETY

The following detailed description of the new variety is based upon observations taken of plants and fruits grown "underglass," i.e., undertunnel, in the farm of La Mogalla in Cartaya (Huelva), Spain, about 7° W, 37° N, 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other known methods of propagating strawberry plants may be used. Strawberries root well after transplanting.

The term "blistering" used herein refers to the texture or rugosity inherent to leaves and is generally a constant characteristic.

GENERAL

'Tudnew' is a short day variety that needs an induction to flowering by chilling, such as occurs at a high elevation nursery (fresh plant) or with cold storage (referred to as a frigo). Usually a short time is sufficient. 'Tudnew' is self-fertile. It produces large quantity of pollen throughout the seasons and pollination is generally good as there are very few malformed fruit.

Production: Plants described are from a high elevation nursery.

Trials pursued in Cartaya (Huelva), Spain.

*Date of planting.*—Oct. 21, 1996.

*Number of repetitions.*—2.

*Plants per repetition.*—100.

Figure 1:
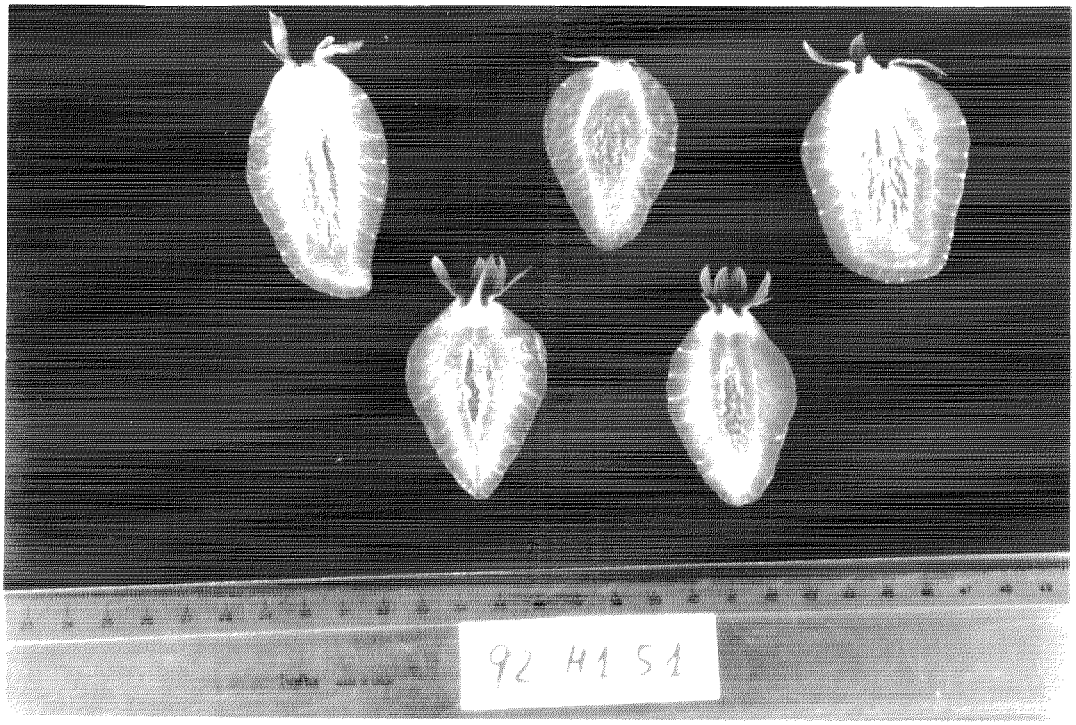
FIG. 1 shows typical fruit in cross section illustrating the typical flesh and flesh coloration, conspicuous core and core cavity and conical shape.
Figure 2:
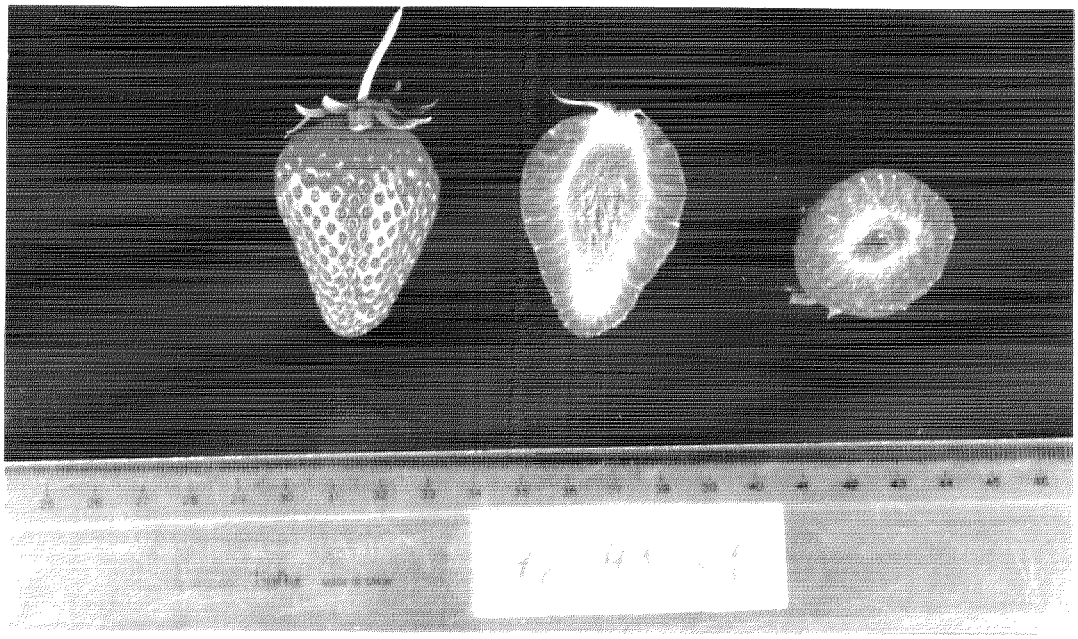
FIG. 2 shows whole and sliced detached fruit.
Figure 3:
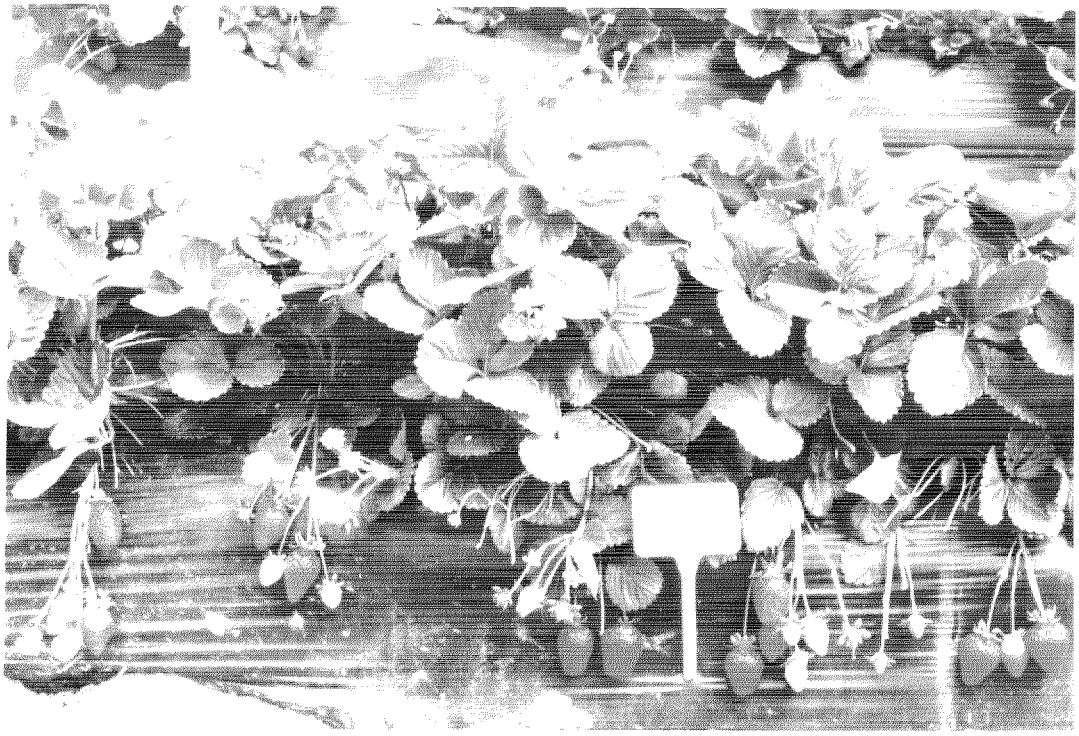
FIGS. 3 and 4 show the fruit against a background of the top surface of the foliage.
Figure 4:
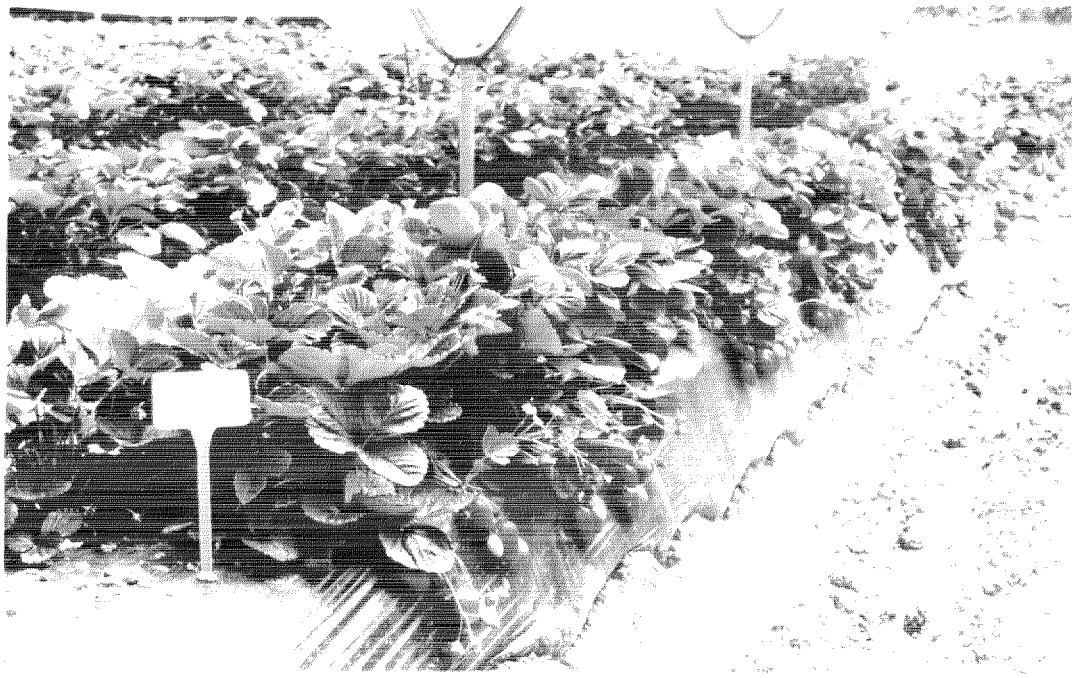
Figure 5:
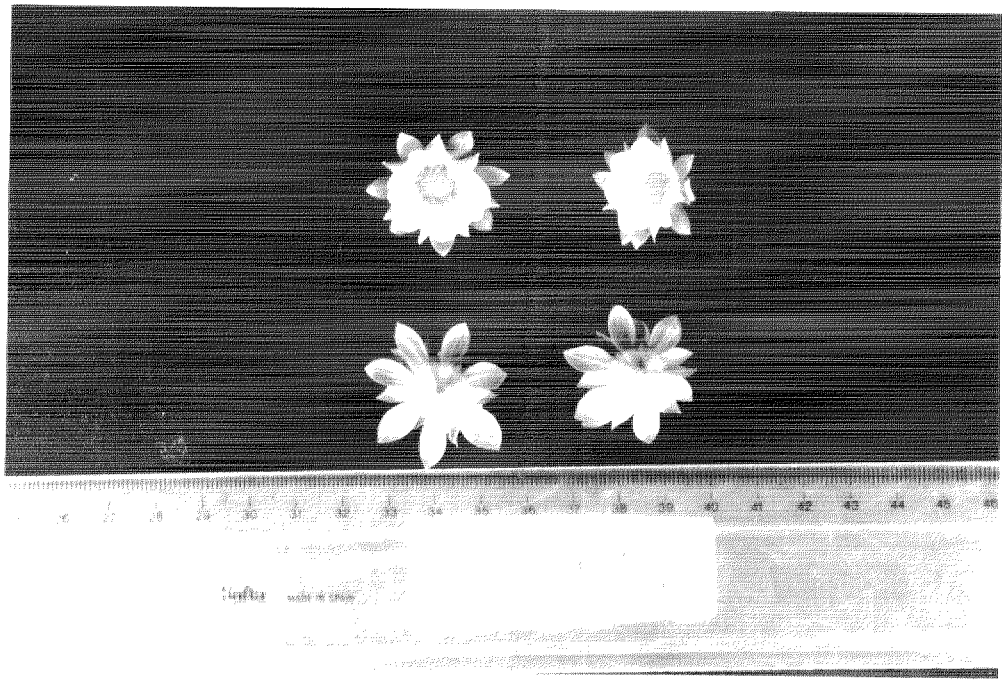
FIG. 5 shows the flower and reproductive organs of the new variety.
Figure 6:
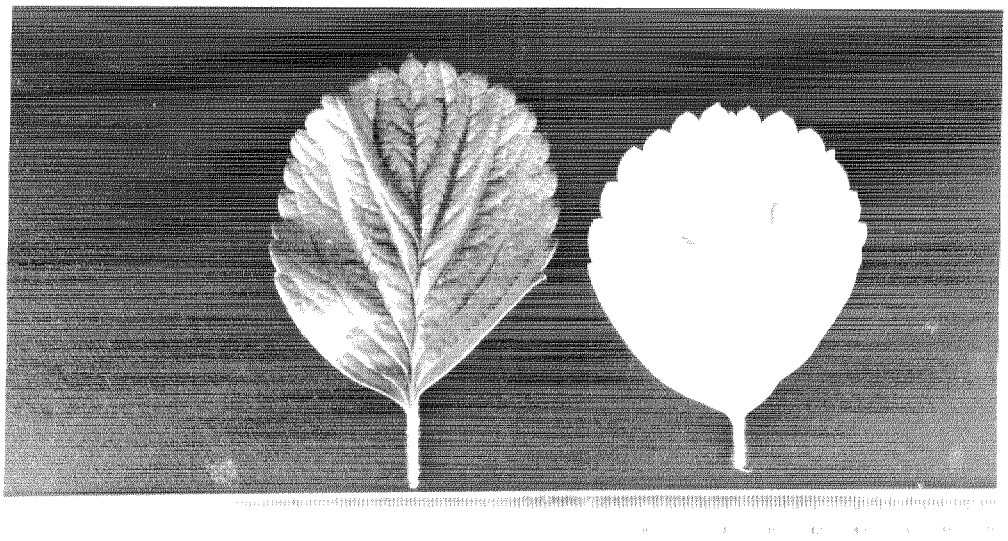
FIG. 6 shows the top and undersurface of a typical foliole of the new variety.
Figure 7:
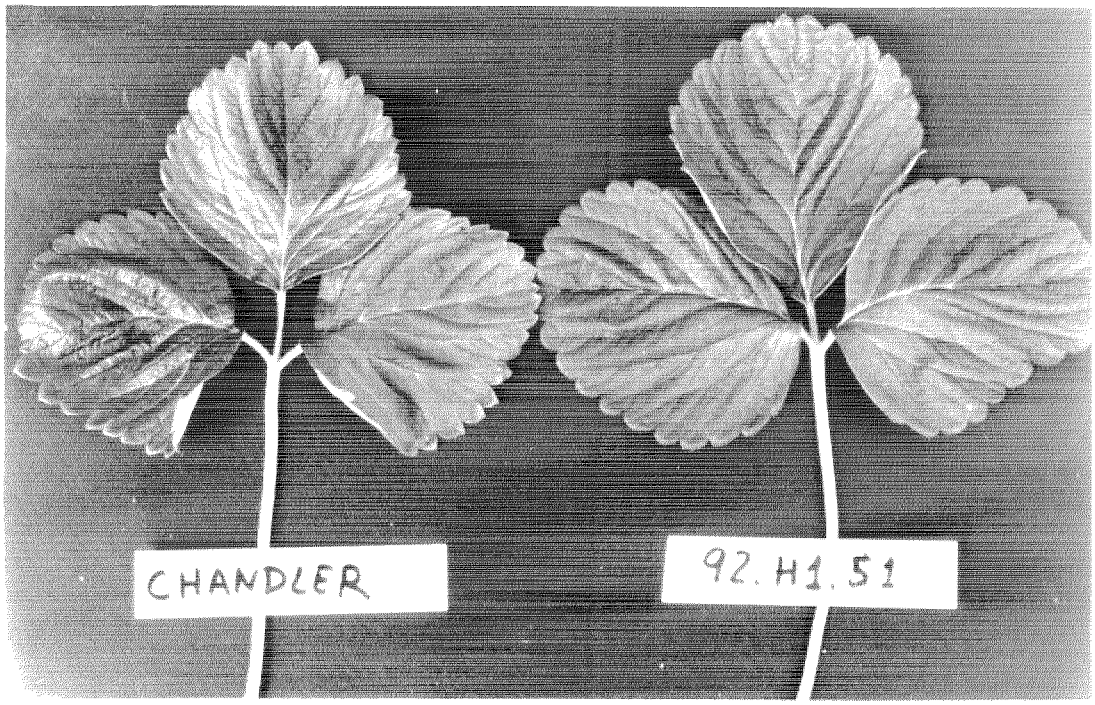
FIG. 7 shows a comparison of the foliage of the new variety (designated 92.H1.51) and of the variety 'Chandler'.
Figure 8:
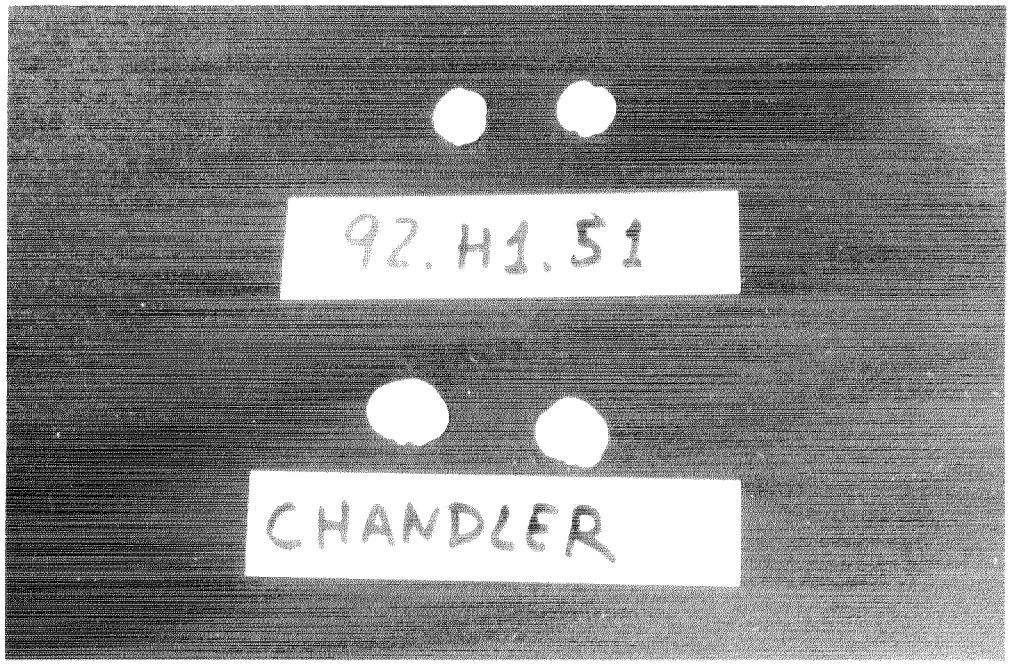
FIG. 8 shows a comparison of the ratio length/width of the petals of the new variety (designated 92.H1.51) and of the variety 'Chandler'.
Figure 9:
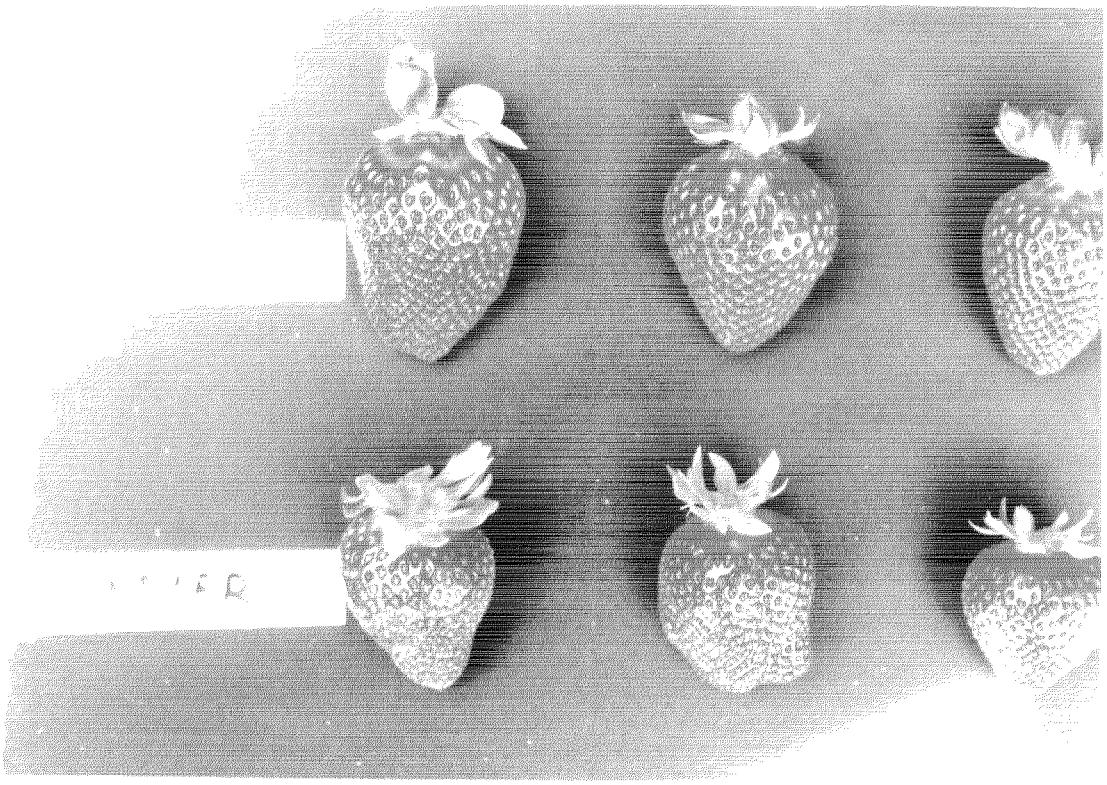
FIG. 9 shows a comparison of the size, shape, band without achenes and pose of the calyx segments of the new variety (designated 92.H1.51) and of the variety 'Chandler.'

*Comparison with 'Chandler'.*—The new variety is compared with 'Chandler' in FIGS. 7, 8, and 9.

Accumulated Production of First Quality Fruit (g/plant)

| Variety | 28 Fb | 31 Mr | 30 Ap | 31 My |
|---|---|---|---|---|
| CARTUNO | 52 | 202 | 376 | 534 |
| MILSEI | 64 | 253 | 447 | 677 |
| OSO GRANDE | 42 | 201 | 419 | 605 |
| ARENA | 57 | 238 | 420 | 584 |
| TUDNEW | 90 | 275 | 471 | 670 |

| Variety | 1st + 2nd Quality Fruit | Total | Weight (g/fruit) |
|---|---|---|---|
| CARTUNO | 534 + 73 | 607 | 23–22 |
| MILSEI | 677 + 110 | 787 | 24–23 |
| OSO GRANDE | 605 + 107 | 712 | 23–22 |
| ARENA | 584 + 120 | 704 | 22 |
| TUDNEW | 670 + 109 | 779 | 24–23 |

Production total, to 31 May, of First Quality Fruit (1st quality) and Second Quality Fruit (2nd quality) in g/plant

| Variety | 1st quality | 2nd quality | TOTAL (1st quality + 2nd quality) | % 2nd quality |
|---|---|---|---|---|
| CARTUNO | 534 | 73 | 607 | 12 |
| MILSEI | 677 | 110 | 787 | 14 |
| OSO GRANDE | 605 | 107 | 712 | 15 |
| ARENA | 584 | 120 | 704 | 17 |
| TUDNEW | 670 | 109 | 779 | 14 |

-continued $$\% \text{ 2nd quality} = \frac{\text{2nd quality}}{\text{TOTAL}} \times 100$$

Size (g/Fruit) at two dates: 31 March and 31 May

| SIZE (g/fruit) | 31 March | 31 May |
|---|---|---|
| CARTUNO | 23 | 22 |
| MILSEI | 24 | 23 |
| OSO GRANDE | 23 | 22 |
| ARENA | 22 | 22 |
| TUDNEW | 24 | 22 |

Fruit Analysis

| | MILSEI | ARENA | CHANDLER |
|---|---|---|---|
| Firmness (KG) | 0.34 | 0.61 | 0.84 |
| Humidity & Volatile Matter (%) | 92.46 | 91.90 | 92.09 |
| Dry Matter (5/%) | 7.54 | 8.10 | 7.91 |
| pH (to 20°) | 3.06 | 3.25 | 3.42 |
| Acidity as Anhydride Citric (%) | 0.96 | 0.80 | 0.83 |
| Soluble Solids (°Brix) | 6.90 | 7.40 | 7.50 |
| Maturity Index | 7.18 | 9.25 | 9.04 |
| Content in Ascorbic Acid (ppm) | 580 | 530 | 520 |
| Luminosity: Transmittance to 460 nm | 41.40 | 38.00 | 30.50 |

| | CARTUNO | OSO GRANDE | TUDNEW |
|---|---|---|---|
| Firmness (KG) | 0.61 | 1.00 | 1.46 |
| Humidity & Volatile Matter (%) | 92.39 | 92.33 | 92.84 |
| Dry Matter (5/%) | 7.61 | 7.67 | 7.16 |
| pH (to 20°) | 3.68 | 3.56 | 3.35 |
| Acidity as Anhydride Citric (%) | 0.58 | 0.61 | 0.80 |
| Soluble Solids (°Brix) | 7.10 | 6.10 | 6.50 |
| Maturity Index | 12.24 | 10.00 | 8.12 |
| Content in Ascorbic Acid (ppm) | 500 | 630 | 650 |
| Luminosity: Transmittance to 460 nm | 47.10 | 40.10 | 17.30 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry matter: It is the weight of the residual left from the trituration of the fruit after the drying process at a temperature of 102° C.±2° C. until reaching constant weight.

$$\% \text{ Dry Matter} = \frac{\text{Weight Dry Matter}}{\text{Weight Fresh Matter}} \times 100$$

Humidity & volatile matter: Represents the content in volatile matters and water of the fruits.

% humidity & volatile Matter=100−% Dry matter.

Maturity index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety.

Variety: 'Tudnew'—Breeder Reference 92.H1.51.
Classification: Fragaria, L.
Plant:
*Habit.*—Flat globose.
*Density.*—Medium.
*Vigor.*—Medium.
*Height.*—About 17 cm.
*Width.*—About 24 cm.
Leaf: Upperside near 138b to 138A; underside near 145D.
*Length.*—About 10 cm.
*Width.*—About 11 cm.
*Cross section.*—Slightly concave.
*Blistering.*—Strong.
*Number of leaflets.*—Three only.
Leaf stem characteristics:
*Color.*—Near 149D.
*Position of hairs.*—Outward.
*Length.*—About 10 cm.
Terminal leaflet:
*Length/width ratio.*—As long as broad.
*Length.*—About 6.5 cm.
*Width.*—About 6.5 cm.
*Shape of base.*—Obtuse.
*Shape of teeth.*—Rounded.
Petiole:
*Position of hairs.*—Outward.
*Length.*—About 10 cm.
Stipule:
*Anthocyanin coloration.*—Absent or very weak.
Stolons:
*Number.*—Many, about 9.
*Anthocyanin coloration.*—Medium
*Thickness.*—Medium, about 3.2 mm.
*Pubescence.*—Weak.
*Color.*—Near 149D to 150D.
Inflorescence:
*Position relative to foliage.*—Above.
Flower:
*Size.*—Large.
*Size of calyx relative to corolla.*—Same size.
*Size of inner calyx relative to outer.*—Same size.
*Spacing of petals.*—Overlapping.
Flower characteristics:
*Diameter primary flowers.*—About 4 cm.
*Diameter secondary flowers.*—About 3 cm.
*Number of petals.*—Normally about 6. No significant fragrance.
*Time from bloom to mature fruit (in Huelva, Spain).*—About 35 to 40 days.
Petal:
*Length/width ratio.*—About as long as broad.
Fruiting truss:
*Attitude.*—Semi-erect.
Fruit:
*Ratio of length/maximum width.*—Much longer than broad.
*Color.*—Near 42A to 42C.
*Peduncle length of inflorescence stem.*—Primary fruit about 9 to 11 cm, secondary fruit about 6 to 7 cm, color near 149D.
Primary fruit:
*Length.*—About 7.5 cm.
*Width.*—About 4.5 cm.
Secondary fruit:
*Length.*—About 5.5 cm.
*Width.*—About 3.5 cm.
*Size.*—Very large.
*Predominant shape.*—Conical.
*Difference in shapes between primary and secondary fruit.*—Slight.
*Band without achenes.*—Broad.
*Unevenness of surface.*—Uneven.
*Color.*—Near 46C.
*Evenness of color.*—Even.
*Glossiness.*—Strong.
*Insertion of achenes.*—Below surface.
*Insertion of calyx.*—Set above fruit.
*Pose of the calyx segments.*—Reflexed.
*Size of calyx in relation to fruit diameter.*—Same size.
*Firmness.*—Very firm.
*Color of flesh.*—Medium red, near 42B; lightening toward center.
*Evenness of color of flesh.*—Even.
*Sweetness.*—Medium.
*Acidity.*—Strong.
*Time of flowering.*—Early.
*Time of ripening.*—Early.
*Type of bearing.*—Not remontant.
*Planting date.*—Oct. 20, 1994.
*10% flowering.*—Dec. 1, 1994.
*First mature fruits.*—Jan. 14, 1994.
*Maturity (15–20 gms/plant).*—Jan. 26, 1994.

Time of flowering data: Date of planting October 20 in the farm of La Mogalla, in Cartaya (Huelva), Spain, about 7°W, 37°N, 45 feet elevation. 10% flowering occurs about December 1 with first mature fruit about January 14 and maturity (15–20 g/plant) about January 26. Time of flowers (50% of plants at first flower) is about December 4.

Storage Qualities: 'Tudnew' fruit maintain their quality characteristics when keeping them in a frigo chamber at temperatures of about 2° C. during 48 hours. The fruit's calyx and epidermis are kept turgid. The Fruit's color remains substantially the same.

Time of ripening: After planting as aforesaid, plants are grown in raised beds undertunnel (small tunnel with small holes on plastic walls). Water and fertilizer were applied through drip irrigation. Time of ripening (50% of plants with ripe fruit) is about January 18. First mature fruit is about January 14 and maturity (size about 15–20 g/plant) is about January 26.

General: The growing period in Huelva, Spain, where the observations were made, is between about January 25 and May 31 of each year, with a maximum production at about mid-April. 'Tudnew' is a short day variety that benefits from induction to flowering by chilling, usually a few hour is sufficient, preferably at temperatures of 7° C. or less. Normally, the minimum number of hours is accumulated in the field during several days.

Disease resistance: No particular sensitivity to any disease or parasite has been observed for 'Tudnew.'

I claim:

1. A new and distinct strawberry plant of the variety substantially as shown and described.

* * * * *

UNITED STATES PATENT AND TRADEMARK OFFICE

CERTIFICATE OF CORRECTION

PATENT NO. : Plant 10,960
DATED : June 15, 1999
INVENTOR(S) : Jose Miguel Arias Lopez It is certified that error appears in the above-identified patent and that said Letters Patent is hereby corrected as shown below:

Column 1, line 12, replace "evaluation" with -- elevation --.
Column 4, line 12, in the Table replace "TUDNEW 24 22" with -- TUDNEW 24 23 --.
Column 6, line 60, replace "hour" with -- hours --.

Signed and Sealed this

Seventeenth Day of April, 2001

*Attest:*

Nicholas P. Godici

NICHOLAS P. GODICI

*Attesting Officer*

*Acting Director of the United States Patent and Trademark Office*